(12) United States Patent
Prom

(10) Patent No.: US 10,973,523 B2
(45) Date of Patent: Apr. 13, 2021

(54) MEDICAL DEVICE FOR TREATING A TARGET SITE

(71) Applicant: AGA Medical Corporation, Plymouth, MN (US)

(72) Inventor: Darren Todd Prom, Coon Rapids, MN (US)

(73) Assignee: AGA Medical Corporation, Plymouth, MN (US)

( * ) Notice: Subject to any disclaimer, the term of this patent is extended or adjusted under 35 U.S.C. 154(b) by 162 days.

(21) Appl. No.: 13/791,337

(22) Filed: Mar. 8, 2013

(65) Prior Publication Data

US 2014/0257361 A1  Sep. 11, 2014

(51) Int. Cl.
 *A61B 17/12* (2006.01)
 *A61B 17/00* (2006.01)

(52) U.S. Cl.
 CPC .. *A61B 17/12022* (2013.01); *A61B 17/12031* (2013.01); *A61B 17/12109* (2013.01); *A61B 17/12172* (2013.01); *A61B 17/12177* (2013.01); *A61B 2017/00477* (2013.01); *A61B 2017/12095* (2013.01)

(58) Field of Classification Search
 CPC ........ A61B 17/12022; A61B 17/12027; A61B 17/12031; A61B 17/12036; A61B 17/1204; A61B 17/12045; A61B 17/12109; A61B 17/12113; A61B 17/12122; A61B 17/12131; A61B 17/12104; A61B 2017/00575; A61B 2017/00606; A61B 2017/00632; A61B 2017/00637; A61B 17/0057; A61B 2017/1205; A61B 2017/12054; A61B 2017/12095; A61F 2/01; A61F 2/013; A61F 2/2442; A61F 2/2427; A61F 2/246
 USPC .......................... 606/200, 211, 213, 214, 218
 See application file for complete search history.

(56) References Cited

U.S. PATENT DOCUMENTS

| | | | |
|---|---|---|---|
| 5,725,552 A * | 3/1998 | Kotula | A61B 17/0057 604/285 |
| 5,733,294 A * | 3/1998 | Forber | A61B 17/12022 606/151 |
| 6,364,895 B1 | 4/2002 | Greenhalgh | |
| 6,371,971 B1 | 4/2002 | Tsugita et al. | |
| 7,442,200 B2 | 10/2008 | Mazzocchi et al. | |
| 8,034,061 B2 | 10/2011 | Amplatz et al. | |

(Continued)

OTHER PUBLICATIONS

Merriam-Webster Dictionary, Definition of lobe, Apr. 2009, https://www.merriam-webster.com/dictionary/lobe (Year: 2009).*

(Continued)

*Primary Examiner* — Todd J Scherbel
*Assistant Examiner* — Mikail A Mannan
(74) *Attorney, Agent, or Firm* — Armstrong Teasdale LLP

(57) ABSTRACT

Embodiments of the present disclosure are directed to medical devices, methods, and systems for delivering a medical device to a target site. In one embodiment, a medical device includes a proximal lobe and a distal lobe, at least one of the proximal lobe or the distal lobe configured to receive a delivery device therethrough. The medical device also includes a central engagement member disposed between the proximal lobe and the distal lobe, the central engagement member configured to be engaged by a delivery device for facilitating deployment of the proximal and distal lobes at the target site.

14 Claims, 12 Drawing Sheets

(56) References Cited

U.S. PATENT DOCUMENTS

| | | | |
|---|---|---|---|
| 8,162,974 B2* | 4/2012 | Eskuri et al. | 606/213 |
| 9,179,899 B2* | 11/2015 | Freudenthal | A61L 31/08 |
| 2002/0111647 A1* | 8/2002 | Khairkhahan et al. | 606/200 |
| 2002/0143349 A1 | 10/2002 | Gifford, III et al. | |
| 2005/0273135 A1 | 12/2005 | Chanduszko et al. | |
| 2005/0288786 A1* | 12/2005 | Chanduszko | A61B 17/0057 623/11.11 |
| 2007/0265656 A1* | 11/2007 | Amplatz | A61B 17/0057 606/200 |
| 2007/0276415 A1* | 11/2007 | Kladakis et al. | 606/151 |
| 2008/0200945 A1* | 8/2008 | Amplatz | A61B 17/12172 606/195 |
| 2009/0018562 A1* | 1/2009 | Amplatz | A61B 17/0057 606/157 |
| 2009/0099647 A1 | 4/2009 | Glimsdale et al. | |
| 2009/0281567 A1* | 11/2009 | Osypka | 606/215 |
| 2011/0082495 A1* | 4/2011 | Ruiz | A61B 17/0057 606/213 |
| 2011/0184452 A1 | 7/2011 | Huynh et al. | |
| 2012/0065667 A1* | 3/2012 | Javois | A61B 17/12122 606/213 |
| 2012/0172973 A1 | 7/2012 | Deckard et al. | |

OTHER PUBLICATIONS

"AMPLATZER™ Multi-Fenestrated Septal Occluder—'Cribriform';" St. Jude Medical; retrieved on Sep. 18, 2012 from <http://www.sjmprofessional.com/Products/US/structural-heart-therapy/amplatzer-cribriform-occluder.aspx>.

Freed, B. H., et al.; "*Percutaneous Transcatheter Closure of the Native Aortic Value to Treat De Novo Aortic Insufficiency After Implantation of a Left Ventricular Assist Device*;" JACC: Cardiovascular Interventions; vol. 5, No. 3; dated 2012.

* cited by examiner

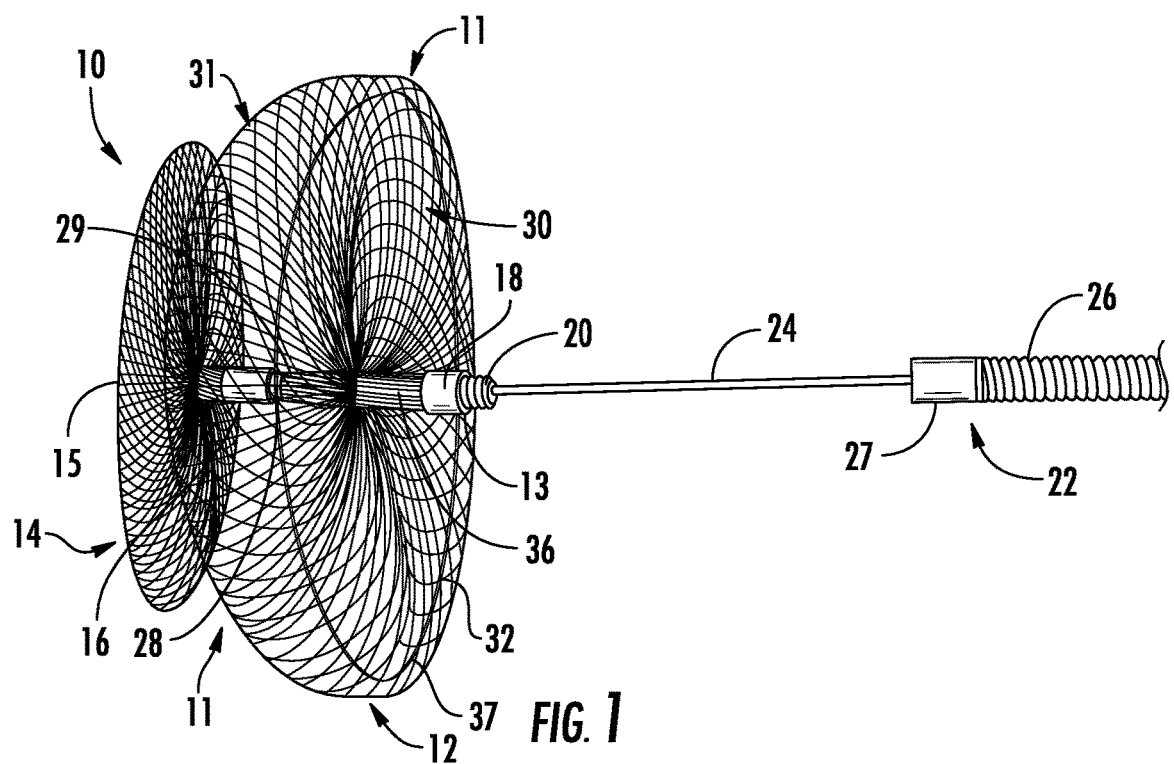
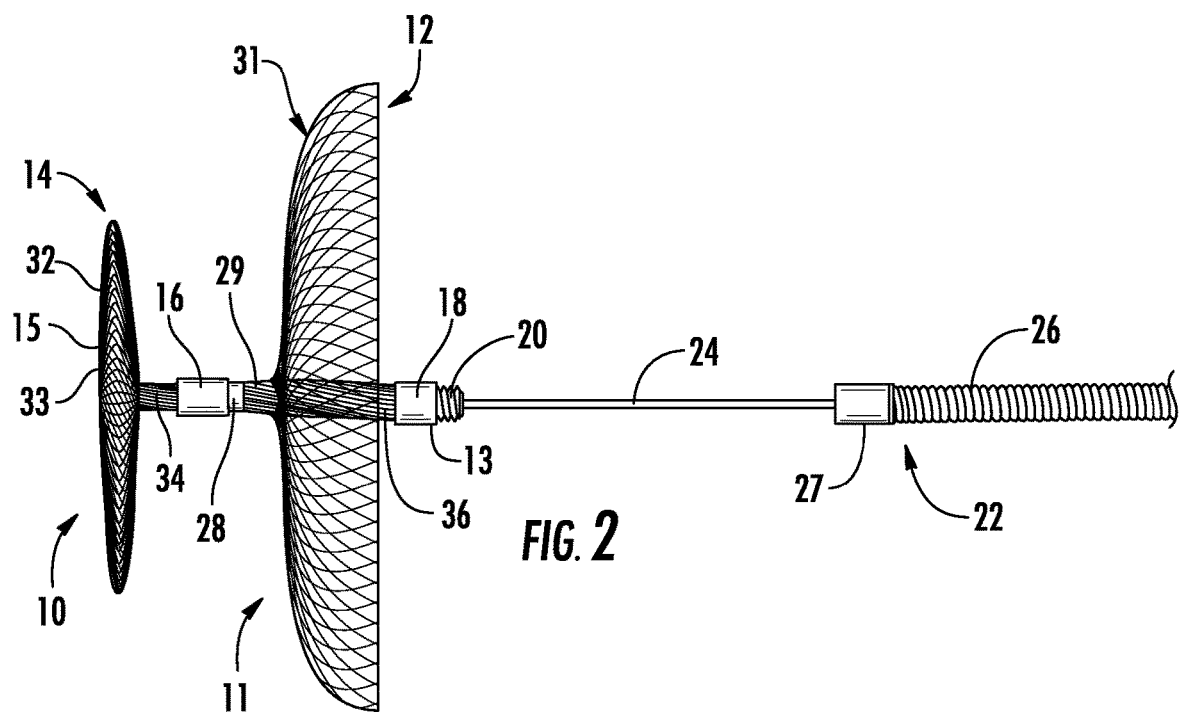

MEDICAL DEVICE FOR TREATING A TARGET SITE

BACKGROUND

I. Field of the Disclosure

The present disclosure relates generally to medical devices for treating target sites. More particularly, the present disclosure is directed to devices, systems, and methods for treating areas within a patient's body, such as an aortic valve.

II. Description of the Related Art

A wide variety of intravascular devices are used in various medical procedures. Certain intravascular devices, such as delivery devices and guidewires, are generally used to deliver fluids or other medical devices to specific locations within a patient's body, such as a select site within the vascular system. Other, frequently more complex medical devices are used to treat specific conditions, such as medical devices used to occlude a target site.

BRIEF SUMMARY

Embodiments of the present disclosure are directed to medical devices, systems, and methods for treating a target site. In one embodiment, a medical device for treating a target site includes a proximal lobe and a distal lobe. At least one of the proximal lobe or the distal lobe is configured to receive a delivery device therethrough. The medical device also includes a central engagement member disposed between the proximal lobe and the distal lobe. The central engagement member is configured to be engaged by a delivery device for facilitating deployment of the proximal and distal lobes at the target site.

According to another embodiment, a medical device for treating a target site includes at least one lobe having a proximal surface, a distal surface, and an outer flange. The at least one lobe has an expanded configuration and is configured to be constrained to a reduced configuration for delivery to the target site. The proximal surface and the outer flange define a concave shape facing in a proximal direction. The at least one lobe comprises at least one layer of braided fabric configured to facilitate long-term occlusion of the target site. The medical device further includes a non-permeable membrane coupled to the at least one lobe and configured to facilitate acute occlusion of the target site.

One embodiment of a method of delivering a medical device includes providing a medical device comprising a central engagement member disposed between a proximal lobe and a distal lobe and attaching the central engagement member to a delivery device. The method further includes advancing the delivery device and medical device in a reduced configuration to the target site and deploying the medical device at the target site such that the medical at least partially returns from the reduced configuration to an expanded configuration. In addition, the method includes detaching the central engagement member from the delivery device and withdrawing the delivery device.

In one embodiment, a system for delivering medical device to a target site is provided. The system includes a medical device comprising a central engagement member disposed between a proximal lobe and a distal lobe. The system also includes a delivery device comprising a coupling member configured to couple to the central engagement member for facilitating deployment of the medical device at the target site.

BRIEF DESCRIPTION OF THE DRAWINGS

The foregoing features and advantages of embodiments in accordance with the present disclosure will become apparent to those skilled in the art from the following detailed description, especially when considered in conjunction with the accompanying drawings in which like numerals in the several views refer to corresponding parts.

FIG. 1 is a perspective view of a medical device in an expanded configuration and a delivery device according to an embodiment of the present disclosure;

FIG. 2 is a side view of the medical device and the delivery device from FIG. 1;

DETAILED DESCRIPTION

Figure 3:
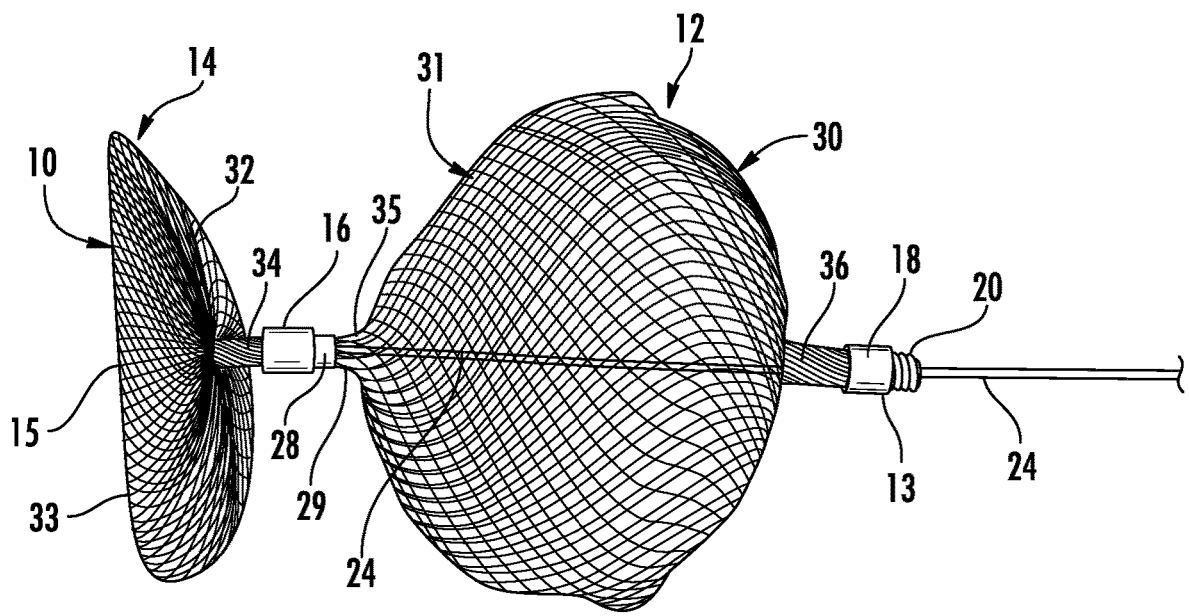
FIG. 3 is a side view of the medical device from FIG. 1 in a partially reduced configuration.

Several factors affect the effectiveness of a medical device to treat a target site, such as the particular geometry and mechanical properties of the medical device. For example, a medical device suitable for treating one target site may be unsuitable for treating another target site. Thus, the geometry of the medical device may be modified to treat a particular target site and to better position the medical device at the target site. In some instances where a target site is to be occluded, slower or faster occlusion time may be necessary in order to effectively occlude a target site. However, additional customization of the medical device and the ability to accurately deploy the medical device at a desired position may be necessary to more effectively treat a target site.

Therefore, it would be advantageous to provide a medical device which offers improved sizing, positioning, and occlusion at the target site.

As described in greater detail below, medical devices in accordance with the present disclosure are configured to treat a target site. In one embodiment, the medical device is configured to be more accurately deployed at the target site in a desired position. The medical device is also configured to be deployed at the target site so as to limit disruption of the anatomy surrounding the target site or injuring the target site. In addition, the medical device is adapted to treat a variety of target sites, and in some instances may facilitate both acute and long-term occlusion. In some embodiments, the medical device may be configured to be locked in an expanded position to improve retention at the target site and to reduce the incidence of migration.

In one embodiment of the present disclosure, the target site is an aortic valve. In this regard, following LVAD (Left Ventricular Assist Device) implantation, the aortic valve may experience aortic insufficiency due to the valve not fully closing and diameter of the aorta may increase over time following LVAD implantation. The medical device is configured to occlude the aortic valve to prevent blood from leaking through the aortic valve in a reverse direction thereby reducing the incidence of regurgitation. When deployed at the aortic valve, the medical device may be configured to engage the sinus of valsalva while limiting any obstruction of the coronary arteries, mitral valve, and nerve bundles. Moreover, the medical device may be configured to immediately occlude the aortic valve while providing minimal disruption of the valve, as well as provide long-term occlusion of the aortic valve. The medical device is also configured to withstand the pressure induced by the LVAD following deployment at the aortic valve. For example, as described in further detail below, the medical device may be configured to clamp opposite sides of the valve to secure the valve leaflets therebetween.

It is understood that the use of the term "target site" is not meant to be limiting, as the medical device may be configured to treat any target site, such as an abnormality, a vessel, an organ, an opening, a chamber, a channel, a passageway, a hole, a cavity, a body lumen, a valve, or the like, located anywhere in the body. The medical device may be suitable for selective occlusion of a target site anywhere in the body's circulatory system where it is desired to stop the flow of blood. The medical device may also be deployed in a variety of manners with respect to a target site, such a proximate or adjacent to the target site, at the target site, or within the target site. Moreover, although examples are provided of a medical device that is used for treating a target site within the circulatory system, such as for the closure of an aortic valve, it is understood that embodiments of the medical device may be used for various applications. In addition, although the medical device is herein described in connection with a delivery device, it is further understood that the medical device may be used with other catheters, delivery sheathes, device loaders, and other accessories. As also used herein, the term "proximal" refers to a portion of the referenced component of a medical device that is closest to the operator, and the term "distal" refers to a portion that is farthest away from the operator at any given time as the medical device is delivered to the target site.

Embodiments of the present disclosure are described more fully hereinafter with reference to the accompanying drawings, in which some, but not all, embodiments are shown. Indeed, the disclosure may be embodied in many different forms and should not be construed as limited to the embodiments set forth herein; rather, these embodiments are provided so that this disclosure will satisfy applicable legal requirements. Like numbers refer to like elements throughout.

Turning now to the specific embodiments set forth in the accompanying drawings. FIGS. 1 and 2 depict one embodiment of medical device 10, which is configured to treat a target site, such as a target site in a patient's body. Embodiments of medical device 10 generally comprise tubular member 11, proximal lobe 12, proximal end 13, distal lobe 14, and distal end 15. Central clamp 16 may be disposed between proximal lobe 12 and distal lobe 14, while proximal end 13 of tubular member 11 may be secured by proximal clamp 18. Proximal clamp 18 may be coupled to proximal engagement member 20. Medical device 10 is coupled to delivery device 22 including inner delivery wire 24 and outer delivery wire 26. Outer delivery wire 26 includes outer coupling member 27 configured to engage engagement member 20, as also detailed below with reference to FIGS. 4 and 4B. Medical device 10 also includes central engagement member 28 at distal end 29 of proximal lobe 12 that is configured to be coupled to proximal lobe 12 and/or distal lobe 14 and engage inner delivery wire 24, as also discussed below with reference to FIGS. 3 and 4A.

Tubular member 11 may be formed of a braided fabric comprising a plurality of braided strands 32 (see e.g., FIGS. 1-4). Although the term "tubular" is used, it is understood that tubular member 11 may be braided into a continuous tubular body, comprise a sheet of material that is formed into a tubular shape, or be otherwise formed. In addition, tubular member 11 may comprise one or more layers of braided fabric. According to one embodiment of the present disclosure, tubular member 11 includes a braided fabric formed of a plurality of strands 32, wherein each strand 32 has a predetermined relative orientation with respect to one another (e.g., a helical braid). Moreover, medical device 10 may comprise a plurality of layers of braided fabric or other occluding material such that the device is capable of at least partially inhibiting blood flow therethrough in order to facilitate the formation of thrombus and epithelialization around medical device 10. For example, tubular member 11 may include one or more layers of permeable membrane (e.g., polyester) disposed within one or both lobes 12, 14. Thus, braided strands 32 and/or permeable membrane may facilitate long-term occlusion of a target site.

As used therein, "long-term" occlusion is generally a period of time sufficient to facilitate thrombotic activity at the target site. For example, the permeability of medical device 10 (e.g., due to braided strands 32 and/or permeable membrane) may be configured to facilitate long-term occlusion via thrombosis, such as by at least partially inhibiting blood flow therethrough in order to facilitate the formation of thrombus and epithelialization around medical device 10. In particular, strands 32 may be braided to have a predetermined pick and pitch to define openings or fenestrations so as to vary the impedance of blood flow therethrough. For instance, the formation of thrombus may result from substantially precluding or impeding flow, or functionally, that blood flow may occur for a short time, e.g., about 3-60 minutes through the braided fabric, but the body's clotting mechanism or protein or other body deposits on the braided strands 32 results in long-term occlusion or flow stoppage after this initial time period. For instance, occlusion may be clinically represented by injecting a contrast media into the upstream lumen of medical device 10 and if no contrast media flows through the wall of medical device 10 after a predetermined period of time as viewed by fluoroscopy or other visualization technique, then the position and occlusion of medical device 10 is adequate.

Strands 32 of a metal fabric used in one embodiment may be formed of a material that is both resilient and that can be heat treated to substantially set a desired preset shape. One class of materials which meets these qualifications is shape memory alloys. One example of a shape memory alloy is Nitinol. It is also understood that medical device 10 may comprise various materials other than Nitinol that have elastic and/or memory properties, such as spring stainless steel, trade named alloys such as Elgiloy®, Hastelloy®, CoCrNi alloys (e.g., trade name Phynox), MP35N®, CoCrMo alloys, or a mixture of metal and polymer fibers. Depending on the individual material selected, the strand 32 diameter, number of strands 32, and pitch may be altered to achieve the desired properties of medical device 10.

Although the term "strand" is discussed herein, "strand" is not meant to be limiting, as it is understood tubular member 11 may comprise one or more wires, cords, fibers, yarns, filaments, cables, threads, or the like, such that these terms may be used interchangeably. Strands 32 may be braided, interwoven, or otherwise combined to define generally tubular member 11. One may solder, braze, weld, coat, glue, clamp, tie or otherwise affix the ends of braided strands 32 together, such as with marker bands or clamps 16, 18 shown in FIGS. 1-4. Thus, although the term "clamp" is used herein, any securement technique or mechanism may be used to secure the ends of strands 32 together to prevent unraveling. Furthermore, distal lobe 14 may only require one clamp 16 for securing each of strands 32 forming distal lobe. In particular, the ends of strands 32 may begin and end at clamp 16 such that an outer surface at distal end 33 of lobe distal 14 is closed and does not require a clamp. However, it is understood that distal end 33 of distal lobe 14 could alternatively include a clamp such that the proximal and distal ends of strands 32 are secured with respective clamps.

Figure 4:
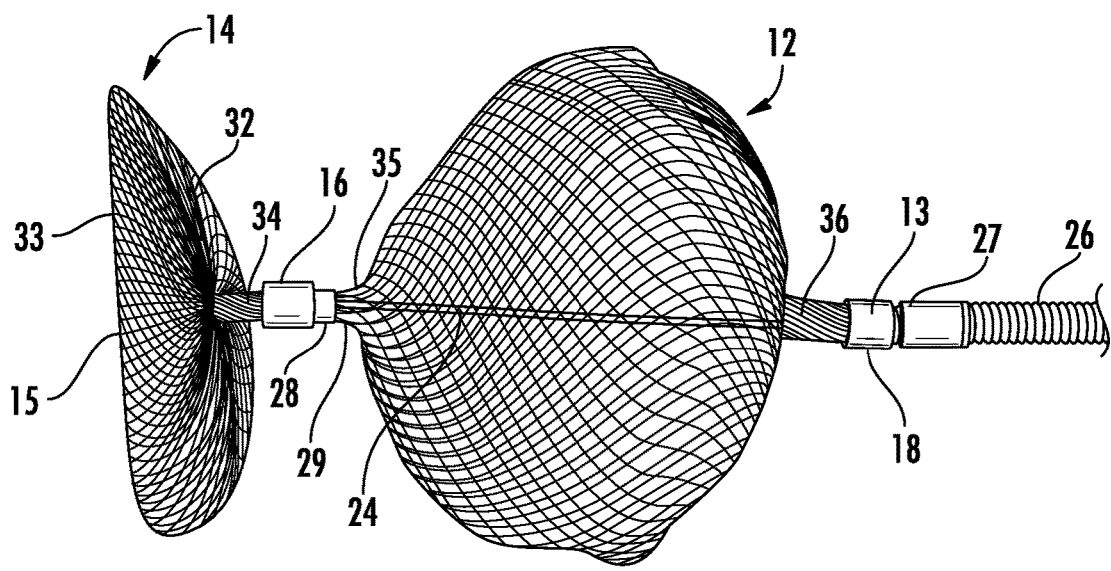
FIG. 4 is a side view of the medical device from FIG. 1 engaged with an outer delivery wire.

FIGS. 2-4 illustrate that proximal strands 34 of distal lobe 14 and distal strands 35 of proximal lobe 12 are gathered together and are configured to be engaged by central clamp 16 and/or central engagement member 28. In one embodiment, proximal strands 34 and distal strands 35 may be separate strands that are coupled together by central clamp 16 and/or central engagement member 28 (see e.g., FIG. 4A). In this way, lobes 12, 14 may have different braid configurations. For example, FIGS. 1 and 2 illustrate that proximal lobe 12 includes a lower pick count than distal lobe 14, wherein a higher pick count provides reduced flexibility. In another embodiment, strands 34, 35 may be continuous and extend through central clamp 16 and central engagement member 28. In other words, tubular member 11 may be a single unitary member formed of a plurality of strands 32, or tubular member 11 may be formed of independently formed lobes 12, 14 that are coupled together. Likewise, proximal strands 36 of proximal lobe 12 may be gathered at proximal end 13 of tubular member 11 and secured by proximal clamp 18 and/or proximal engagement member 20.

Figure 29:
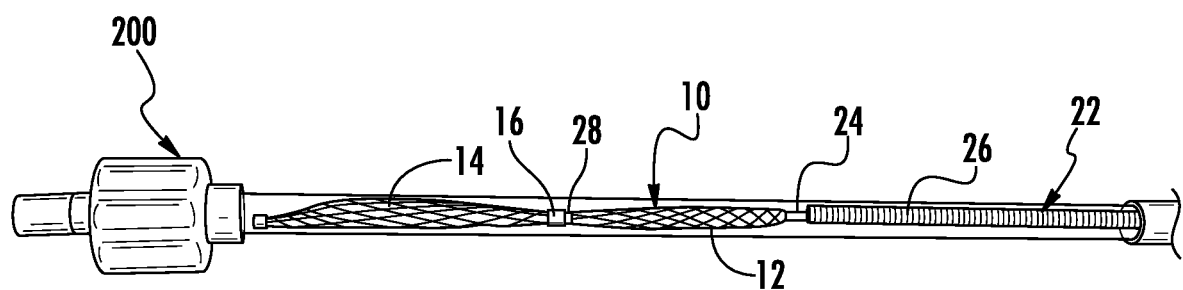
FIG. 29 is a schematic illustration of a delivery system according to one embodiment of the present disclosure.

Tubular member 11 may have a preset configuration, such as an expanded configuration, whereby lobes 12, 14 are configured to be constrained to a reduced configuration for delivery to a target site and at least partially return to the preset configuration upon deployment. For example, tubular member 11 may be heat set in a particular configuration and if formed of a shape-memory material, may be biased such that tubular member 11 is configured to self expand from the reduced configuration and return towards the preset configuration. FIG. 29 shows medical tubular member 11 in a reduced and fully constrained configuration within delivery catheter 30. FIGS. 3 and 4 illustrate tubular member 11 in a partially reduced configuration with proximal 13 and distal 15 ends displaced away from one another. Thus, as proximal 13 and distal 15 ends are displaced from one another and lip 37 is everted, proximal surface 30 of proximal lobe 12 assumes a convex shape. Likewise, the proximal and distal surfaces of distal lobe 12 may be displaced away from one another when proximal 13 and distal 15 ends are displaced away from one another. Removal of the constraint (e.g. delivery catheter) allows tubular member 11 to return to its expanded configuration shown in FIGS. 1 and 2. One method of delivering medical device 10 is described in more detail with reference to FIG. 30.

Figure 9:
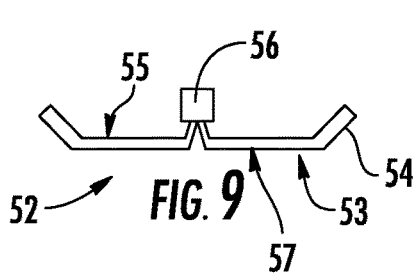
FIG. 9 is a schematic cross-sectional illustration of a medical device according to one embodiment of the present disclosure.

As used herein, the term "lobe" is not meant to be limiting and may be a member having a disk, a circular, an oval, a cylinder, a conical, a frustoconical, a discoid, or other shape having a cross-sectional dimension configured to overlie or engage a target site, such as for substantially precluding or impeding flow through an opening at the target site. For example, FIGS. 1 and 2 illustrate lobes 12, 14 having a generally circular cross-sectional shape, with proximal lobe 12 having a larger outer diameter than distal lobe 14. FIGS. 1 and 2 further illustrate that proximal lobe 12 may include a proximal surface 30 and a distal surface 31. Proximal surface 30 may extend inwardly and be inverted with respect to an outer perimeter of lobe 12 and distally toward distal end 15 to define lip 37, though this curvature could also be reversed for particular applications. Distal surface 31 may have a convex curvature. Thus, lip 37 defines a thin double-walled structure or flange having a concave shape extending about the circumference of proximal lobe 12, which provides increased radial strength about proximal lobe 12. Likewise, distal lobe 14 may include a similar convex curvature as that of proximal lobe 12 in some embodiments, or reversed curvature (i.e., convex proximal surface and concave distal surface), or may lack curvature and appear substantially flat or disk shaped. Although FIGS. 1 and 2 illustrate tubular member 11 with proximal lobe 14 and distal lobe 12, it is understood that tubular member 11 may have one or any number of more lobes 12, 14 depending on the target site and particular application (see e.g., FIG. 9).

Figure 4A:
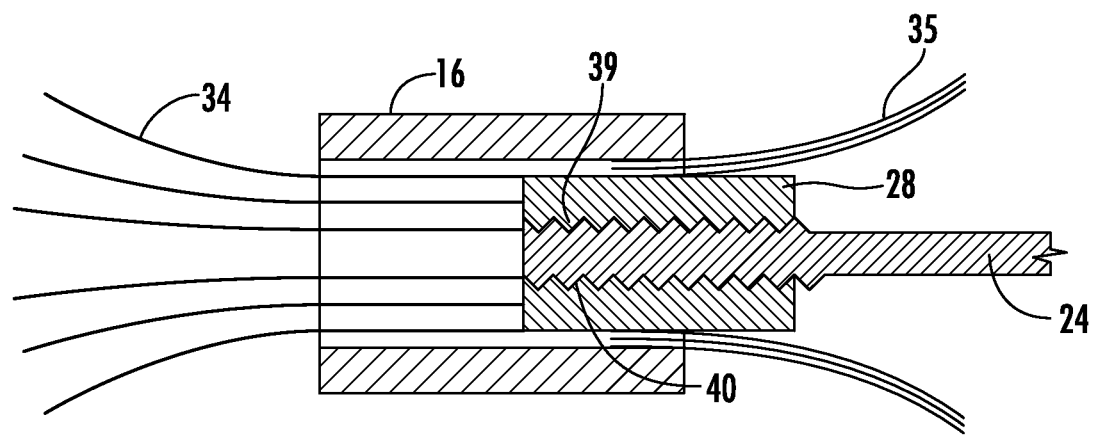
FIG. 4A is an enlarged cross-sectional view of a central engagement member of the medical device from FIG. 1 engaged with an inner delivery wire.

FIG. 4A illustrates an enlarged view of central engagement member 28 in engagement with coupling member 40 of inner delivery wire 24. As shown, proximal strands 34 of distal lobe 14 and distal strands 35 of proximal lobe 12 extend within, and are secured by, clamp 16. Central engagement member 28 is disposed between lobes 12, 14 and may be coupled to distal end 29 of proximal lobe 12. Central engagement member 28 may be attached to central clamp 16 (e.g., welding, adhesives, or press fit connection), although central engagement member 28 and central clamp 16 could be integrally formed as a single component in one embodiment. Central engagement member 28 may be configured to releasably attach to inner delivery wire 24. In this regard, FIG. 4A shows that central engagement member 28 may have threaded internal bore 39 or surface that is sized and configured for receiving externally threaded coupling member 40. Thus, central engagement member 28 may be configured as an internally threaded end screw for receiving coupling member 40 of inner delivery wire 24 in a threaded engagement such that rotation of inner delivery wire 24 in a clockwise or counterclockwise direction facilitates attachment to and detachment from central engagement member 28 depending on the direction in which inner delivery wire 24 is rotated. It is understood that the illustrated engagement between central engagement member 28 and coupling member 40 is not meant to be limiting, as the threads may be reversed such that central engagement member 28 is externally threaded and coupling member 40 is internally threaded. Furthermore, other suitable techniques may be used to engage and disengage coupling member 40 from central engagement member 28 in response to manipulation of inner delivery wire 24 while providing the ability to transmit torque, such as a press fit, snap fit, twist-fit, and the like.

FIG. 4A also illustrates that in one embodiment, proximal strands 34 of distal lobe 14 and/or distal strands 35 of proximal lobe 12 may be affixed to an external surface of central engagement member 28 and internally within central clamp 16. The strands 34 and/or 35 may be secured, such as with swaging or welding of clamp 16, whereby strands 34 and/or 35 are secured between clamp 16 and central engagement member 28. However, as noted above, the strands 34 and/or 35 may be secured with other techniques and in other configurations.

Central engagement member 28 may facilitate more accurate deployment at a target site. In this regard, when engaged with inner delivery wire 24, central engagement member 28 and/or central clamp 16 may be used by an operator to visualize the position of medical device 10 at the target site, such as where central engagement member 28 and/or central clamp 16 are formed of a radiopaque material. For example, the operator may align central engagement member 28 with an opening of the aortic valve so that lobes 12, 14 will be deployed on opposite sides of the valve opening. Moreover, manipulation of inner delivery wire 24 while engaged with central engagement member 28 may also facilitate deployment of medical device 10 where medical device 10 is deployed using a "pin-pull" technique. For instance, inner delivery wire 24, while engaged with central engagement member 28, may be maintained stationary while an outer delivery catheter is withdrawn to unsheathe medical device 10 and allow medical device 10 to expand from its constrained configuration towards its expanded configuration. Thus, engagement between inner delivery wire 24 and central engagement member 28 may allow medical device 10 to be securely positioned at a desired location while being deployed.

Figure 4B:
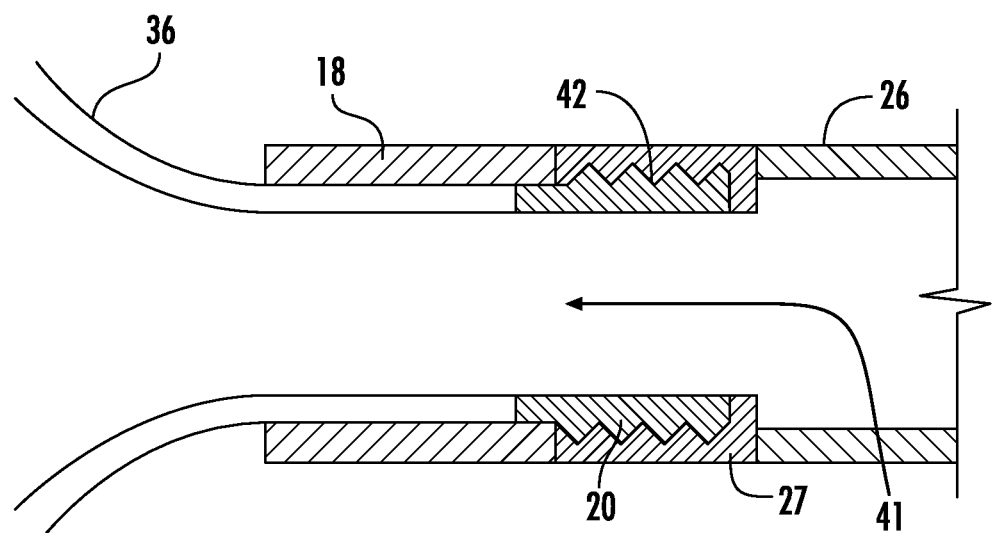
FIG. 4B is an enlarged cross-sectional view of a proximal end of the medical device from FIG. 3 engaged with an outer delivery wire.

FIG. 4B shows an enlarged view of proximal clamp 18 coupled to proximal engagement member 20. FIG. 4B also illustrates that proximal strands 36 are configured to be gathered and secured within proximal clamp 18. Proximal clamp 18 and proximal engagement member 20 further define an opening 41 therethrough. Inner delivery wire 24 and associated coupling member 40 are configured to be axially displaced through opening 41 for engaging central engagement member 28 (see FIG. 4A). Should medical device 10 need to be recaptured prior to being fully deployed or after being detached from inner delivery wire 24, FIGS. 4 and 4B show that outer delivery wire 26 may include outer coupling member 27 configured to releasably attach to proximal engagement member 20. Recapture may thus be possible in some embodiments through the use of outer delivery wire 26 and outer coupling member 27 as long as either inner delivery wire 4 or outer delivery wire 26 is still attached, allowing the medical device 10 to be removed and/or redeployed. Attachment of outer coupling member 27 to proximal engagement member 20 facilitates a secure engagement so that inner delivery wire 24 can be withdrawn. In particular, FIG. 4B illustrates that outer coupling member 27 may include internal threads 42 configured to threadably engage and disengage externally threaded proximal engagement member 20 depending on the direction in which outer delivery wire 26 is rotated. Thus, in one embodiment, proximal engagement member 20 may be configured as an end screw with at least a portion having an externally threaded surface. In addition, other suitable techniques may be used to engage and disengage outer coupling member 27 from proximal engagement member 20 in response to manipulation of outer delivery wire 26 while providing the ability to transmit torque, such as a press fit, snap fit, twist-fit, and the like. Moreover, the threaded engagement between outer coupling member 27 and proximal engagement member 20 could be reversed if desired such that outer coupling member 27 is externally threaded and proximal engagement member 20 is internally threaded.

Figure 5:
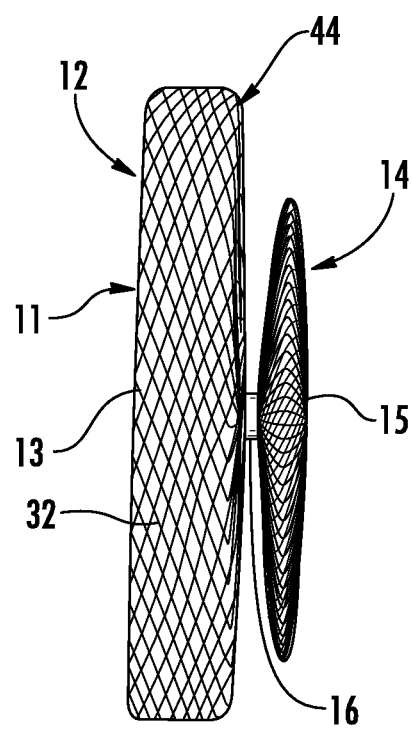
FIG. 5 is a side view of a medical device according to another embodiment of the present disclosure.
Figure 6:
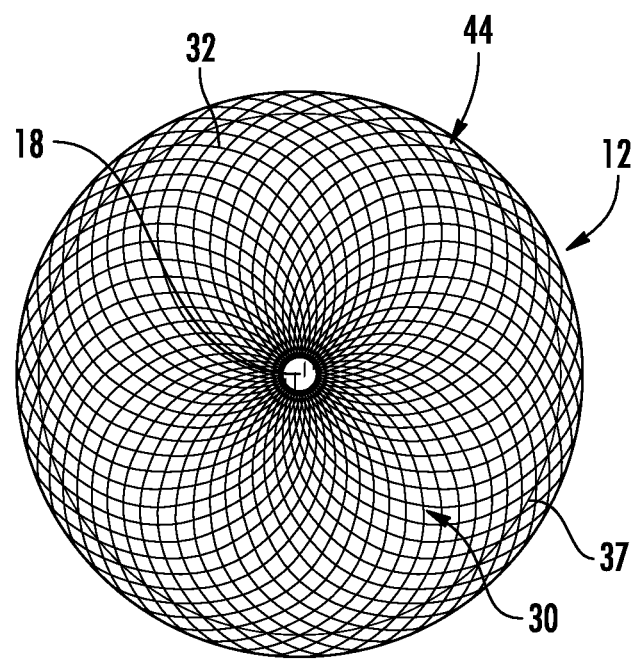
FIG. 6 is an end view of the medical device from FIG. 5.

FIGS. 5 and 6 illustrate an additional embodiment of medical device 44. In this regard, medical device 44 includes tubular member 11 formed of strands 32, proximal lobe 12, distal lobe 14, proximal end 13, and distal end 15. Similar to FIGS. 1-4 above, medical device 44 also includes central clamp 16 disposed between lobes 12, 14, as well as proximal clamp 18 at proximal end 13. Although not shown, central clamp 16 could include or be coupled to an engagement member, such as engagement member 20. Moreover, FIGS. 5 and 6 illustrate an embodiment where proximal lobe 12 has a cylindrical outer surface with lip 37 defined about the outer circumference of lobe 12. Thus, medical device 44 also includes proximal surface 30 having a concave shape. Distal lobe 14 is generally disk shaped, although as discussed above, lobes 12, 14 may have any desired shape. FIG. 5 also shows that the distance between lobes 12, 14 may vary, with lobes 12, 14 in FIGS. 1 and 2 being farther apart than lobes 12, 14 shown in FIGS. 5 and 6. For example, the distance between lobes 12, 14 may be between approximately 0 mm to approximately 10 mm. Thus, the distance between lobes 12, 14 may be varied depending on the target site to be treated, as well as the amount of clamping force desired between lobes. For example, the distance between lobes 12, 14 may be shortened to achieve a greater clamping force at the target site.

Figure 7:
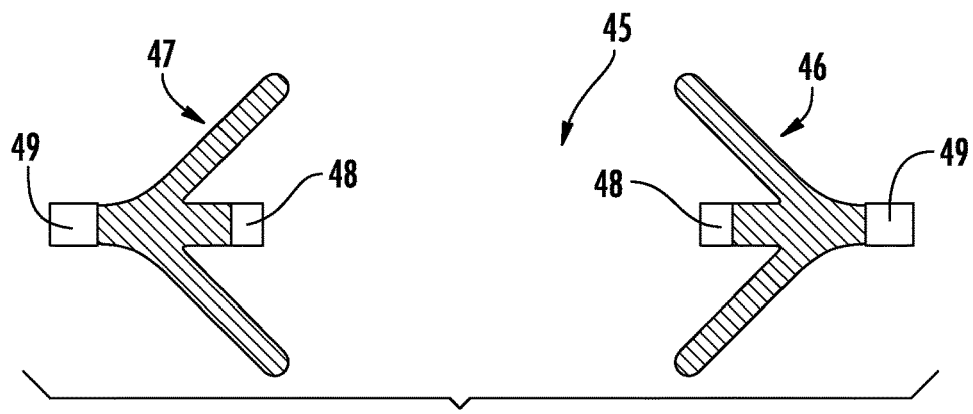
FIG. 7 is a schematic cross-sectional illustration of a medical device according to another embodiment of the present disclosure.

FIG. 7 illustrates medical device 45 according to another embodiment of the present disclosure. In this regard, medical device 45 includes first lobe 46 and second lobe 47 that are configured to be coupled to one another. Thus, lobes 46, 47 may be modular components that are configured to releasably attach to one another. Lobes 46, 47 may be coupled together with respective central clamps 48 such as with a threaded, twist, force, and/or welded fitting. Lobes 46, 47 are generally conical in shape although other shapes may be used. In addition, lobes 46, 47 are shown as being angled towards one another such that central clamps 48 are at least partially surrounded by lobes 46, 47. Although lobes 46, 47 are shown as having the same size and shape, in some embodiments, lobes 46, 47 may be different sizes or shapes and/or possess the same or different mechanical properties. Moreover, each lobe 46, 47 may include respective end clamps 49 that are configured to secure the ends of a respective lobe 46, 47 as well as engage a delivery device for delivering medical device 45 to a target site. Where medical device 45 is formed of braided strands, such as braided strands discussed above with reference to FIGS. 1-4, clamps 49 may be configured to secure the free ends of the strands. In addition, due to the modular configuration of medical device 45, each lobe 46, 47 may include a different braid configuration or pattern (e.g., number of strands, pitch of strands, pick count, diameter of strands, etc.). The stiffness of lobes 46, 47 may be adjusted, for example, to mitigate erosion, auxiliary occlusion, nerve bundle pinching, etc., while at the same time balancing the effect of the selected stiffness on migration/embolization and primary occlusion, by varying parameters including the strand diameter, pitch angle, number of strands, and/or heat set parameters of the material. For example, where medical device 45 is used to treat an aortic valve, a softer braid could be used for first lobe 46 positioned within the heart, while a stiffer braid for second lobe 47 could be used outside of the heart.

Figure 8:
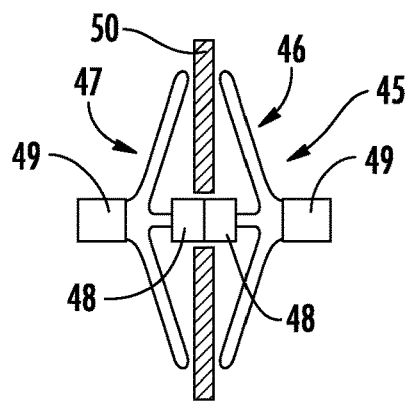
FIG. 8 is a schematic illustration of the medical device from FIG. 7 deployed at a target site.

FIG. 8 shows medical device 45 deployed at target site 50, wherein target site 50 includes an opening defined through a membrane. In this example, medical device 45 is shown in an expanded configuration wherein first lobe 46 and second lobe 47 are in engagement with the membrane on opposite sides of target site 50, and central clamps 48 are positioned at least partially within the opening of target site 50. In the expanded configuration, lobes 46, 47 may be biased towards one another such that medical device 45 is configured to provide a clamping force on the membrane of target site 50, which may be a thin membrane or heart valve. This clamping force can be seen by comparing FIGS. 7 and 8 in that lobes 46, 47 have been collapsed towards one another, wherein the angle defined within each lobe 46, 47 has been reduced or otherwise "flattened".

In another embodiment of the present disclosure, FIGS. 9-12 illustrate medical device 52 including single lobe 53. In this particular embodiment, lobe 53 includes outer flange 54, as well as proximal surface 55, to which clamp 56 is coupled, and distal surface 57. Proximal surface 55 may be concave in configuration such that flange 54 and proximal surface 55 cooperate to define a concave basin. Namely, flange 54 is angled in a distal-to-proximal direction from proximal surface 55 such that lobe 53 defines a concave shape facing the proximal direction towards clamp 56.

Figure 10:
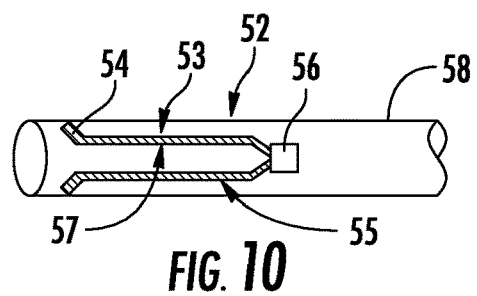
FIG. 10 is a schematic illustration of the medical device from FIG. 9 disposed within a delivery catheter in a reduced configuration.
Figure 11:
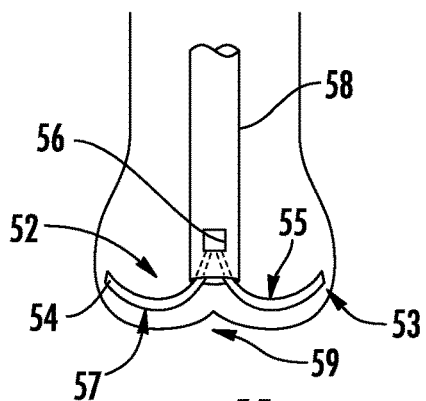
FIG. 11 is a schematic illustration of the medical device from FIG. 9 in a partially deployed state at a target site.
Figure 12:
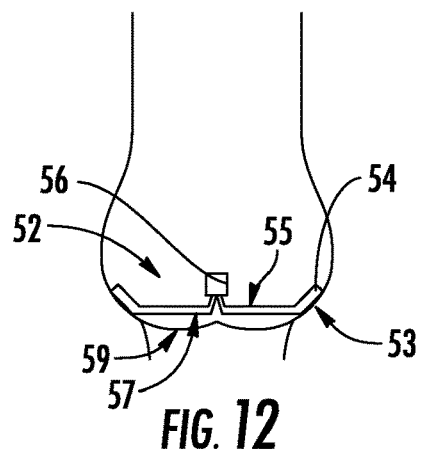
FIG. 12 is a schematic illustration of the medical device from FIG. 9 in a deployed state at the target site.

FIGS. 10-12 illustrate an embodiment whereby medical device 52 is delivered within delivery catheter 58 to target site 59, such as an aortic valve. In this regard, FIG. 10 shows that lobe 53 may be collapsed to a reduced configuration for positioning within delivery catheter 58. For example, lobe 53 may be constrained such that flange 54 is displaced in a distal direction away from clamp 56, thereby assuming a reduced diameter. FIG. 11 illustrates medical device 52 partially deployed at target site 59 where it can be seen that flange 54 expands outwardly towards target site 59. In this regard, flange 54 is partially displaced from the distal end of delivery catheter 58 such that flange 54 is allowed to outwardly expand. In FIG. 12, medical device 52 is shown in a fully deployed position where medical device 52 is secured within target site 59 via engagement of flange 54 with target site 59. Thus, medical device 52 is able to expand towards its initial shape when released from delivery catheter 58. When deployed at target site 59 such as the aortic valve, the concave shape allows medical device 52 to hug the sinus of valsalva and minimize the axial elongation of medical device 52 to reduce or eliminate obstruction of the left and right coronary arteries, mitral valve, and nerve bundles. Namely, flange 54 is configured to align and engage with the sinus of valsalva to limit the axial elongation that would otherwise occur if lobe 53 did not include flange 54 and the device was allowed to freely expand. In the illustrated embodiment, concave proximal surface 55 is facing upstream of the aortic valve such that medical device 52 is further secured at aortic valve due to blood pressure acting on medical device 52 in a distal direction.

Figure 13:
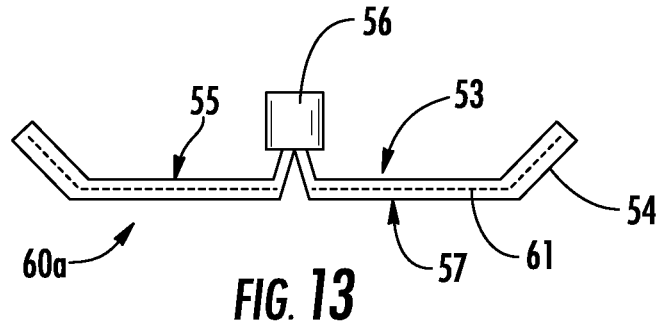
FIG. 13 is a schematic cross-sectional illustration of a medical device including a non-permeable membrane disposed within a lobe according to one embodiment of the present disclosure.
Figure 14:
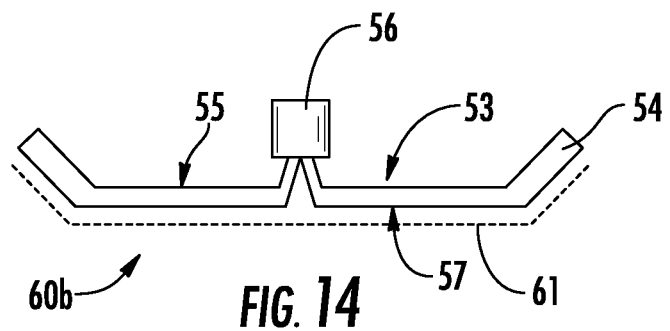
FIG. 14 is a schematic cross-sectional illustration of a medical device including a non-permeable membrane coupled to a distal surface of a lobe according to one embodiment of the present disclosure.
Figure 15:
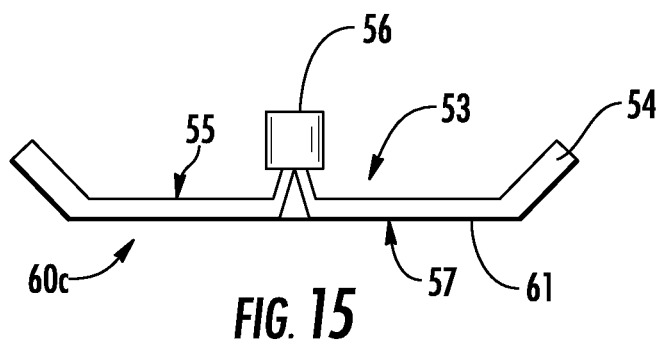
FIG. 15 is a schematic cross-sectional illustration of a medical device including a non-permeable membrane on a distal surface of a lobe according to one embodiment of the present disclosure.

FIGS. 13-15 illustrate additional embodiments of medical device 60a, 60b, 60c. Each embodiment of medical device 60a, 60b, 60c illustrated in FIGS. 13-15 includes single lobe 53 having proximal surface 55 and distal surface 57, although more than one lobe 53 may be employed in alternative embodiments. Medical devices 60a, 60b, 60c may include proximal clamp 56 for securing braided strands and/or coupling to a delivery device as discussed above with reference to FIGS. 1-4. Similar to the embodiment of medical device 52 shown in FIGS. 9-12, medical device 60a, 60b, 60c may include flange 54. As shown in FIG. 13, medical device 60a includes non-permeable membrane 61 coupled to lobe 53. In particular, non-permeable membrane 61 is disposed within lobe 53 such that non-permeable membrane 61 is positioned between proximal surface 55 and distal surface 57. In this way, non-permeable membrane is protected since it is disposed between proximal 55 and distal 57 surfaces. FIG. 14 illustrates that non-permeable membrane 61 could be coupled to distal surface 57, which may facilitate occlusion of medical device 60b at the target site. For example, by having membrane 61 on distal surface 57, membrane 61 is in direct contact with the clinical surface and allows for a "seal" with the surface to encourage better acute occlusion. FIG. 15 shows non-permeable membrane 61 is a coating on distal surface 57 of medical device 60c.

Thus, non-permeable membrane 61 may be secured to lobe 53 using any suitable technique, such as with adhesives, sewing, or fasteners, or as a coating directly on lobe 53.

Non-permeable membrane 61 may be configured to facilitate acute occlusion of the target site. In this regard, "acute" occlusion may include occlusion that occurs rapidly or immediately when medical device 60a, 60b, 60c is deployed at a target site. Thus, acute occlusion is generally a shorter period of time than long-term occlusion. For example, acute occlusion may be in some embodiments about 5 minutes or less, about 4 minutes or less, about 3 minutes or less, about 2 minutes or less, about 1 minute or less, about 30 seconds or less, about 15 seconds or less, about 10 seconds or less, or about 5 seconds or less. Non-permeable membrane 61 may be formed of a variety of non-permeable or non-porous materials, such as a polymer sheet or coating (e.g., polyurethane) or natural tissue (e.g., collagen). In addition to non-permeable membrane 61, flange 54 may also facilitate acute occlusion by conforming to the shape of the target site and further sealing medical device 60a, 60b, 60c at the target site. In addition, although medical device 60 is described as including non-permeable membrane 61, one would appreciate that non-permeable membrane 61 may alternatively be a permeable or semi-permeable membrane in some embodiments. As discussed above with reference to FIGS. 1-4, permeable membrane may facilitate long-term occlusion of the target site. Indeed, medical device 60a, 60b, 60c may include both non-permeable membrane 61 and permeable membrane if desired. In addition, as also discussed above, medical lobe 53 may be formed of a plurality of strands, such as braided strand 32 described above with reference to FIGS. 1-4 for facilitating long-term occlusion at a target site whereby thrombotic activity occurs at the target site.

Figure 16:
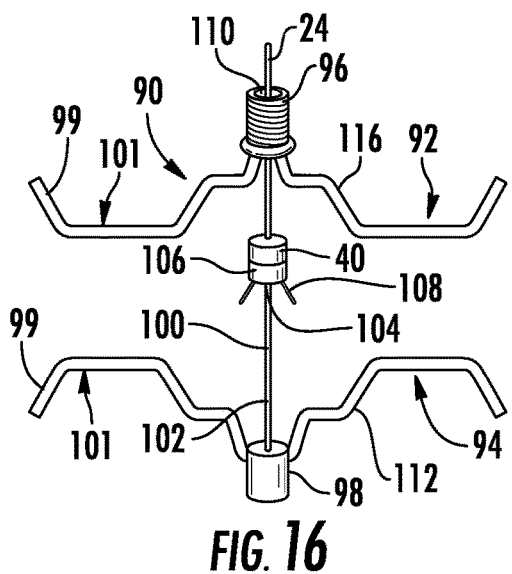
FIG. 16 is a schematic illustration of a medical device engaged with an inner delivery wire according to one embodiment of the present disclosure.

FIG. 16 shows another embodiment of medical device 90, wherein FIGS. 17-20 illustrate in further detail each of the components shown in FIG. 16. Medical device 90 generally includes proximal lobe 92 and distal lobe 94, with each lobe including a respective clamp, proximal clamp 96 and distal clamp 98. Lobes 92, 94 are shown in FIG. 16 as being minor images of one another, with each lobe 92, 94 having a generally concave shape. In this particular embodiment, each lobe 92, 94 includes outer flange 99 extending from surface 101 that is angled to define a concave shape extending about the circumference of lobes 92, 94. In this regard, flange 99 at the proximal end is angled in a distal-to-proximal direction such that flange 99 and surface 101 define a concave shape facing a proximal direction towards proximal clamp 96. Similarly, flange 99 at a distal end is angled in a proximal-to-distal direction such that flange 99 and surface 101 define a concave shape facing in a distal direction towards distal clamp 98.

Lobes 92, 94 may be different sizes and shapes, with proximal lobe 92 having a larger outer diameter than distal lobe 94. For example, the outer diameter of proximal lobe 92 may be about 1-3 mm (about 0.039-0.118 inches) larger than distal lobe 94 in one embodiment. In one embodiment, proximal lobe 92 may be positioned on a first side of an aortic valve (i.e., outside of the heart), while distal lobe 94 is configured to be positioned on a second side (i.e., inside the heart), opposite the first side, of the aortic valve such that the aortic valve is disposed therebetween. The aortic valve may be sandwiched between lobes 92, 94 due to the appropriate tether 100 length and biasing of lobes 92, 94 towards one another in a clamping configuration to provide stability and securement when deployed. As such, the lobes 92, 94 may provide secure placement to occlude the aortic valve to prevent blood from leaking through the aortic valve in a reverse direction thereby reducing the incidence of regurgitation.

FIG. 16 shows inner delivery wire 24 with coupling member 40, similar to inner delivery wire 24 and coupling member 40 described above in connection with FIGS. 1-4A. Inner delivery wire 24 with coupling member 40 are configured to engage engagement member 106. For example, FIG. 16 illustrates that proximal clamp 96 includes opening 110 defined therethrough such that inner delivery wire 24 and coupling member 40 are configured to be displaced through opening 110.

Figure 17:
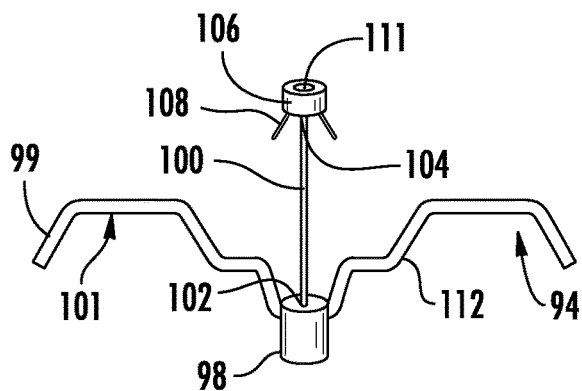
FIG. 17 is an enlarged schematic cross-sectional illustration of a distal lobe from FIG. 16.

FIG. 17 illustrates distal lobe 94 in more detail. In particular, distal lobe 94 further includes protruding central member 112. Thus, central member 112 extends distally from surface 101 towards distal clamp 98. FIG. 17 further illustrates tether 100 comprising first fixed end 102 and second free end 104. First fixed end 102 is coupled to distal clamp 98, and second free end 104 is coupled to engagement member 106. Second free end 104 is configured to be disposed between lobes 92, 94 in an expanded configuration. Engagement member 106 is configured to engage proximal clamp 96 such that medical device 90 is locked in an expanded configuration. At least one spoke 108 is engaged with engagement member 106 and extends outwardly in a proximal-to-distal direction for engaging proximal clamp 96, as shown and described in conjunction with FIG. 19 below.

Figure 18:
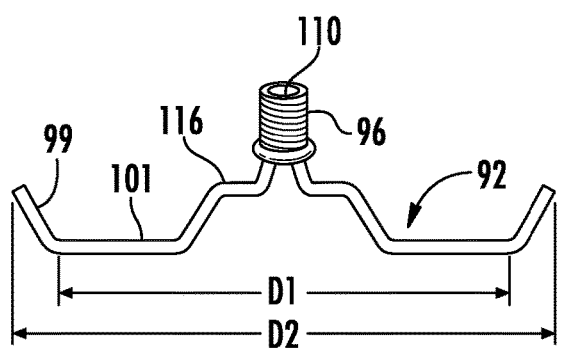
FIG. 18 a schematic cross-sectional illustration of a proximal lobe from FIG. 16.

FIG. 18 illustrates proximal lobe 92 shown in FIG. 16 in more detail. Proximal lobe 92 further includes protruding central member 116. Thus, central member 116 extends outwardly from surface 101 towards clamp 96 in a proximal direction. The size and shape of proximal lobe 92 facilitates positioning at a target site such as an aortic valve, wherein the surface 101 and central member 116 are facing upstream. In this regard, central member 116 may allow for constant pressure to be applied at the target site when deployed. In particular, the use of a "bubble" and concave shape may serve to redistribute the clamping force farther away from the center of the target site so as to allow for a more constant pressure to be applied. In addition, diameter ("D1"), which corresponds to the diameter where flange 99 intersects surface 101, is smaller than outer diameter ("D2") of lobe 92. With respect to use at the aortic valve, D1 may correspond to the diameter of the annulus, while D2 may be sized slightly larger for securing lobe 92 at the aortic valve. For example, D1 may be chosen such that flange 99 engages the sinus of valvasa, while surface 101 aligns with the aortic valve (see e.g., FIG. 12). In one embodiment, D2 may be at least about 5-10 mm (about 0.197-0.394 inches) larger than D1 and/or the diameter of the annulus.

Medical device 90 may have a preset configuration and be configured to be constrained to a reduced configuration for delivery to a target site and at least partially return to its preset configuration. For example, medical device 90 may be heat set in a particular configuration and if formed of a shape-memory material, may be constrained to a reduced configuration (e.g., by axial elongation) and biased such medical device is configured to self expand from the reduced configuration and return towards the preset configuration in a relaxed state. Thus, when medical device 90 is compressed from the preset configuration towards the expanded configuration, a maximum outer diameter of lobes 92, 94 will expand further than in the preset configuration and lobes 92, 94 will be moved towards one another. In addition, because medical device 90 is naturally biased towards the preset configuration when relaxed, medical device will be locked in position due to engagement of spoke 108 with proximal clamp 96 when in the expanded configuration (see FIG. 20).

Figure 19:
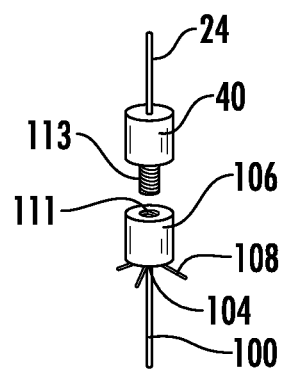
FIG. 19 is an enlarged schematic illustration of an engagement member and the delivery device from FIG. 16 disengaged from one another.

FIG. 19 shows inner delivery wire 24 with coupling member 40, wherein inner delivery wire 24 with coupling member 40 is configured to engage engagement member 106. Coupling member 40 has a smaller outer diameter than the inner diameter of opening 110 such that coupling member 40 and associated inner delivery wire 24 are sized for displacement through opening 110. As such, opening 110 allows coupling member 40 and inner delivery wire 24 to be axially displaced through opening 110. FIG. 19 shows that engagement member 106 may include internal threads 111 configured to engage external threads 113, although other securement techniques are possible for releasably attaching engagement member 106 and coupling member 40. In some embodiments, outer delivery wire 26 may be configured to engage proximal clamp 96 for recapturing medical device 90, as explained above (see e.g., FIG. 4B). For example, proximal clamp 96 may include external threads configured to engage a threaded coupling member 27 of outer delivery wire 26 (see e.g., FIGS. 16, 18, and 20).

Tether 100 may comprise a flexible material and in some embodiments, tether 100 may, for example, be a solid wire and may comprise Nitinol or other super elastic or metal alloy material (e.g., stainless steel). However, in other cases, tether 100 could be one or more wires, cords, fibers, yarns, filaments, cables, threads, or the like. Fixed end 102 of tether 100 is secured to distal clamp 98, such as via a clamp, marker band, welding, or other securement feature. Free end 104 of tether 100 is configured to be axially displaceable through opening 110 defined through proximal clamp 96, as shown in FIG. 16. For example, proximal clamp 96 may define through opening 110 that allows tether 100 to be axially displaced as medical device 90 is moved between a preset configuration and an expanded, locked configuration. In addition, engagement member 106 and spokes 108 are also configured to be displaced through opening 110. Tether 100 may have a length that approximates a desired length between proximal and distal ends of medical device 90 in the expanded, locked configuration. FIG. 16 shows that tether 100 has a length that is less than a length between clamps 96, 98 in a relaxed configuration.

Figure 20:
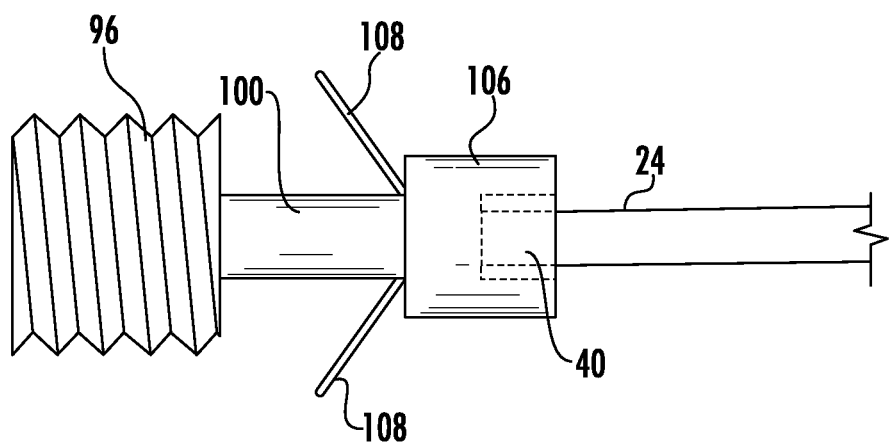
FIG. 20 is an enlarged schematic illustration of the engagement member and the delivery device from FIG. 16 engaged with one another.

Tether 100 comprises at least one spoke 108. As shown in FIG. 20, spoke 108 is coupled to, and extends radially outward from, engagement member 106 and is configured to engage proximal clamp 96 to lock medical device 90 in an expanded configuration. For example, spoke 108 may be biased into contact with clamp 96. Thus, each spoke 108 has a length sufficient to extend from engagement member 106 and engage proximal clamp 96 and is of sufficient strength to lock medical device 90 in the expanded configuration without spoke 108 being deformed or otherwise distorted. Therefore, in the locked, expanded configuration, engagement of spoke 108 and proximal clamp 96 restrains displacement of lobes 92, 94 away from one another due to the tendency of lobes 92, 94 to return to their preset configuration. Spoke 108 may be attached to engagement member 106 using any suitable securement technique, such as swaging or welding. Moreover, the term "spoke" is not meant to be limiting as spoke 108 could be any suitable resilient member configured to lock medical device 90 in the expanded configuration in accordance with the above-described embodiments.

According to some embodiments, tether 100 comprises any number of spokes 108, such as 1 spoke, 2-3 spokes, 2-4 spokes, 2-5 spokes, 2-6 spokes, 2-7 spokes, 2-8 spokes, 2-9 spokes, or 2-10 spokes. Thus, medical device 90 may include any number of spokes 108 for facilitating engagement with clamp 96. Spoke 108 may be formed from a flexible and shape-memory material (e.g., Nitinol) such that spoke 108 is configured to be flexed from an expanded position to a constrained position for displacement through proximal clamp 96 and is biased to naturally return to the expanded position for engaging proximal clamp 96 when unconstrained. Furthermore, FIGS. 16, 18, and 19 show that each spoke 108 may be oriented in an outward, proximal-to-distal direction. This orientation facilitates displacement of spoke 108 through proximal clamp 96, as spoke 108 will be biased towards tether 100 as spoke is displaced through proximal clamp 96. In addition, a proximal-to-distal orientation of spoke 108 in its expanded position facilitates locking engagement with proximal clamp 96 since spoke resists displacement of lobes 92, 94 away from one another. Thus, in the expanded, locked configuration, lobes 92, 94 are configured to provide a clamping force therebetween and to secure medical device 70 at the target site.

Figure 21:
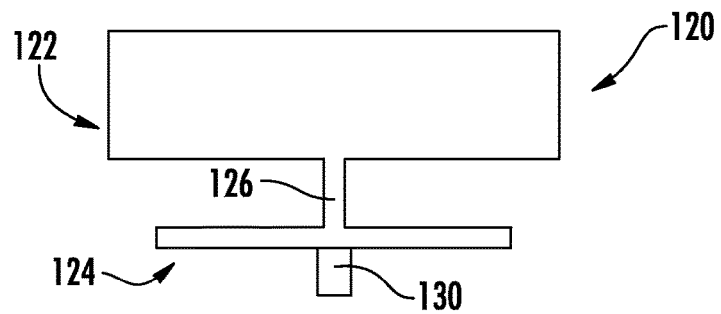
FIG. 21 is a schematic illustration of a medical device including a proximal lobe and a distal lobe according to one embodiment of the present disclosure.
Figure 22:
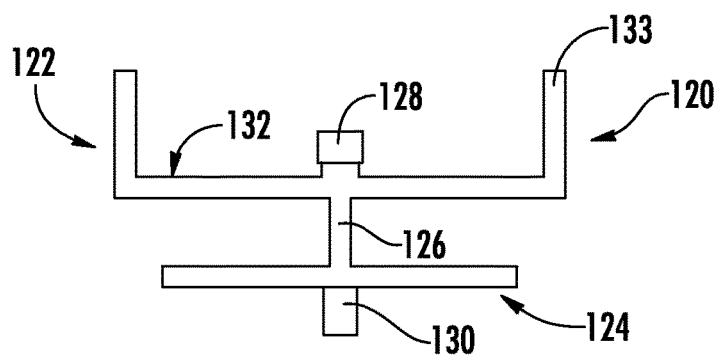
FIG. 22 is a cross-sectional view of the medical device from FIG. 21.

FIGS. 21 and 22 illustrate another embodiment of the present disclosure. Medical device 120 includes proximal lobe 122 and distal lobe 124 coupled with a central waist 126. Each lobe 122, 124 may include a respective clamp, proximal clamp 128 and distal clamp 130. As shown in the cross-sectional view of FIG. 22, proximal lobe 122 may have a concave shape defined by surface 132 and radial flange 133. In this regard, FIG. 22 shows that surface 132 is located distally with respect to clamp 128, while radial flange extends proximally from surface 132 towards clamp 128. Thus, in contrast to a cylindrical-shaped lobe having a single-layer construction, proximal lobe 122 includes a lip defining a double-layer construction due to the concave configuration of flange 133 and surface 132, which provides additional radial rigidity (see also FIGS. 1 and 6). In addition, the layers may be formed from the same piece of material, such as a single tubular member 11 discussed in conjunction with FIGS. 1-4 above.

Figure 23:
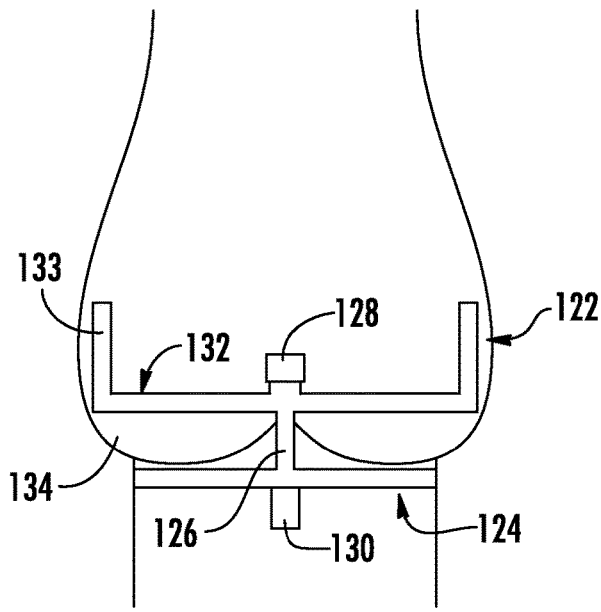
FIG. 23 is a schematic illustration of the medical device from FIG. 22 in an ideal deployed state at the target site.
Figure 24:
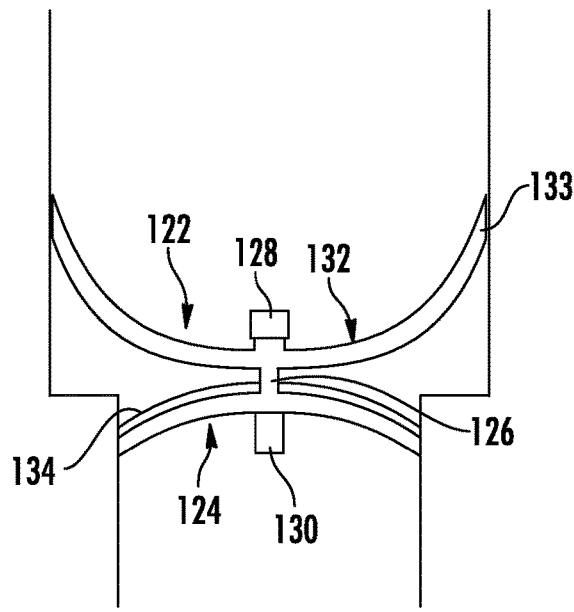
FIG. 24 is a schematic illustration of the medical device from FIG. 22 in a deployed state at the target site.

As shown in FIGS. 23 and 24, medical device 120 is configured for placement for treating aortic valve 134. In particular, proximal lobe 122 is configured for placement on a proximal side of aortic valve 134 (i.e., outside the heart), while distal lobe 124 is configured for placement on a distal side, opposite the proximal side, of aortic valve 134 (i.e., inside the heart). Waist 126 is sized and configured for placement through aortic valve 134. Although it may be desirable to size and configure waist 126 to have a snug fit through aortic valve 134, at the same time waist 126 should not be so tightly engaged with aortic valve 134 as to risk damage to the closed valve, disrupt the partially sealed nature of the valve, and/or disrupt any deposited plaque. FIG. 23 shows an unchanged configuration of medical device 120 at aortic valve with medical device 120 maintaining its preset expanded configuration following deployment. In a more likely scenario, FIG. 24 illustrates a possible configuration of medical device 120 wherein proximal lobe 122 and distal lobe 124 obtain a curved or somewhat distorted shape following deployment, e.g., based on the shape and condition of the actual anatomy of the patient's heart. In this regard, surface 132 and radial flange 133 are shown in FIG. 24 as coextensive with one another, while distal lobe 124 is shown as having a concave curvature in a distal direction.

In some embodiments, proximal lobe 122 has a larger diameter than distal lobe 124, which may be particularly suitable for placement at the aortic valve as discussed above with reference to FIGS. 1-6, 21, and 22. For example, an outer diameter of proximal lobe 122 may be about 30-40 mm (about 1.18-1.57 inches), while an outer diameter of distal lobe 124 may be about 25-30 mm (about 0.984-1.57 inches). The outer diameters of proximal lobe 122 and distal lobe 124 are typically larger than inner diameters of the target site in which medical device 120 is deployed in order to facilitate fixation therein. For example, the outer diameter of each of proximal lobe 122 and distal lobe 124 may be about 10-20% larger than the inner diameter of the target site in which it is deployed. In addition, the length of waist 126 may be varied to correspondingly vary the amount of clamping force between proximal lobe 122 and distal lobe 124, wherein a shorter waist results in an increased clamping force. For instance, the length of waist 126 may be about 3-4 mm (about 0.118-0.157 inches). Moreover, the length of flange 133 may also be varied for providing sufficient engagement with the target site while limiting obstruction of surrounding tissue and vasculature. For example, the length of flange 133 may be about 3-6 mm (about 0.118-0.236 inches) in one embodiment. With reference to FIG. 24, flange 133 may span proximally about 20-25 mm (about 0.787-0.984 inches) from the location of aortic valve 134, while distal lobe 124 may span distally about 5-10 mm (about 0.197-0.394 inches) from the location of aortic valve 134.

Figure 25:
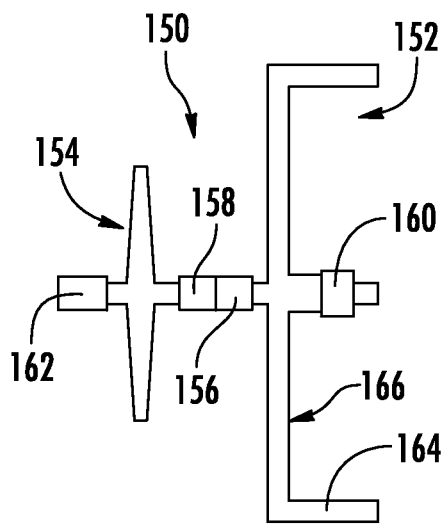
FIG. 25 is a schematic cross-sectional illustration of a medical device including a proximal lobe and a disk-shaped distal lobe coupled to one another according to one embodiment of the present disclosure.
Figure 26:
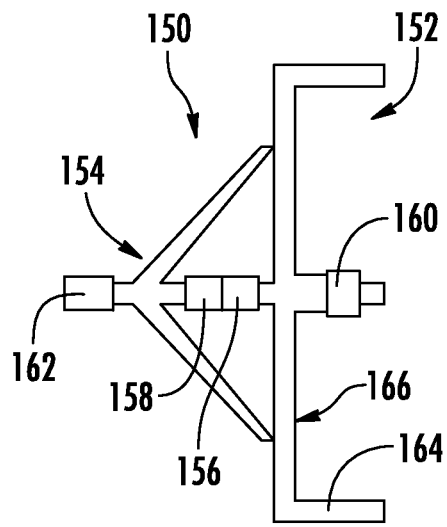
FIG. 26 is a schematic cross-sectional illustration of a medical device including a proximal lobe and a conical-shaped distal lobe coupled to one another according to one embodiment of the present disclosure.

A further embodiment of medical device 150 is shown in FIGS. 25 and 26. As discussed above with reference to FIGS. 7-8, some embodiments provide for medical devices having modular components. FIGS. 25 and 26 illustrate medical device 150 with proximal lobe 152 and distal lobe 154 that are configured to be coupled to one another with respective central engagement members 156, 158, proximal engagement member 156 and distal engagement member 158. Thus, lobes 152, 154 may be customizable to have the same or different geometric or mechanical properties for treating a target site, such as those described above in connection with FIGS. 1-4. Similar to embodiments described above (e.g., FIGS. 1-4), each lobe 152, 154 may include respective clamps 160, 162, proximal clamp 160 and distal clamp 162, at the proximal and distal ends of medical device 150. Similar to medical device 120 shown in FIGS. 21 and 22, proximal lobe 152 may include radial flange 164 and surface 166 that define a concave shape. Similar to FIGS. 21 and 22 discussed above, proximal lobe 152 may define a lip about its circumference due to the concave configuration of radial flange 164 and surface 166 (see also FIGS. 1 and 6). FIGS. 25 and 26 illustrate that distal lobe 154 may have various shapes, such as disk-shaped (FIG. 25) or conical-shaped (FIG. 26), among many different possible shapes (e.g., a circular, an oval, a cylinder, a frustoconical, or a discoid shape). Similar to the embodiment of medical device 10 described above with reference to FIGS. 1-4, proximal lobe 152 may have a larger outer diameter than distal lobe 154.

Figure 27:
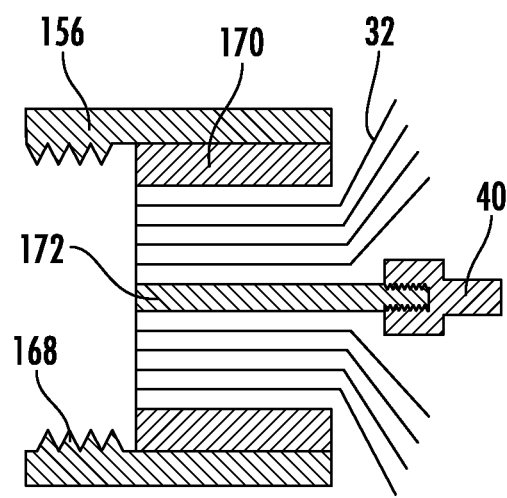
FIG. 27 is an enlarged cross-sectional illustration of a coupling member in engagement with a central engagement member of the medical device from FIGS. 25 and 26.

FIG. 27 shows a detailed view of proximal engagement member 156, which is configured to be coupled to coupling member 40 of inner delivery wire (not shown), such as inner delivery wire 24 discussed above with reference to FIGS. 1-4. Proximal engagement member 156 is shown as having internal threads 168 at its distal end for engaging an externally threaded proximal end of distal engagement member 158. Thus, engagement members 156, 158 may be releasably attached to one another to allow for different sized and shaped lobes 152, 154 to be releasably attached to one another. It is understood that engagement members 156, 158 may be coupled to one another using various securement techniques and mechanisms such that the illustrated embodiment is not meant to be limiting. Furthermore, FIG. 27 shows that in the case where proximal lobe 152 is formed a plurality of braided strands 32, strands 32 may be secured together with radial force from first clamp 170. Likewise, clamp 170 may be any securement device configured to secure strands 32 together and prevent the strands from unraveling. Moreover, clamp 170 may be attached to proximal engagement member 156 or in some instances, strands 32 may be secured directly to proximal engagement member 156 or located between proximal engagement member 156 and clamp 170. Moreover, clamp 170 and proximal engagement member 156 may be an integral component in some embodiments.

As further shown in FIG. 27, proximal engagement member 156 may also include a coupling member 172 that is configured to be attached to coupling member 40 of an inner delivery wire (not shown). Coupling member 172 may provide an offset to allow coupling member 40 to be attached. In this regard, coupling member 172 may be attached to first clamp 170 and/or strands 32 through swaging, adhesive, welding, or other attachment mechanisms. As discussed above with reference to FIGS. 1-4A, proximal engagement member 156 may facilitate more accurate deployment at a target site. In this regard, when engaged with the inner delivery wire, proximal engagement member 156 may be used by an operator to visualize the position of medical device 150 at the target site. Moreover, manipulation of the inner delivery wire while engaged with proximal engagement member 156 may also facilitate deployment of medical device where medical device is deployed using a "pin-pull" technique, discussed above in connection with FIG. 4A.

Figure 28:
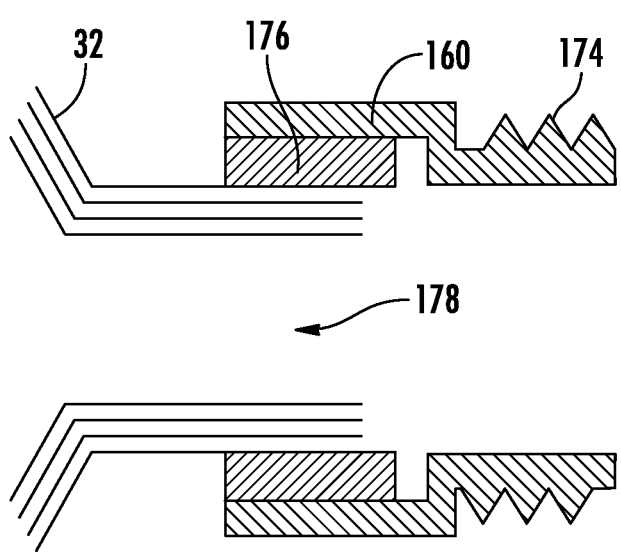
FIG. 28 is an enlarged cross-sectional illustration of a proximal end of the medical device from FIGS. 25 and 26.

FIG. 28 illustrates a detailed view of proximal or second clamp 160 which includes external threads 174 configured to engage a coupling member of an outer delivery wire (see e.g., FIG. 4B) in an instance where medical device 150 is be recaptured. FIG. 28 also shows that strands 32 of proximal lobe may be secured within second clamp 160. For example, one may solder, braze, weld, coat, glue, clamp, or tie strands 32, or strands 32 may be affixed to clamp 160, such as with marker bands or clamps. Thus, the ends of strands 32 may be secured within second clamp 160 by attachment to marker band 176 or the like to prevent strands 32 from unraveling. However, second clamp 160 and marker band 176 may be an integral component in some embodiments, or second clamp 160 may be configured to directly secure strands 32 such that marker band 176 is omitted. In addition, through hole 178 is defined through second clamp 160 such that the inner delivery wire and associated coupling member 40 (shown in FIG. 27) are configured to be displaced through hole 178 for engaging and disengaging central engagement member 156. The hole 178 is also defined through the ends of strands 32. As shown, coupling member 40 has a smaller outer diameter than the inner diameter of hole 178 such that coupling member 40 and associated inner delivery wire are sized for displacement through hole 178. As such, hole 178 allows coupling member 40 and inner delivery wire to be axially displaced through hole 178 as medical device 150 is moved between a reduced configuration and an expanded, locked configuration.

FIG. 29 illustrates an embodiment of a system for delivering a medical device to a target site, such as medical device 10 discussed above with respect to FIGS. 1-4. In this regard, medical device 10 may have an expanded preset configuration (see e.g., FIGS. 1-2). FIG. 29 shows medical device 10 coupled to inner delivery wire 24, and each of medical device 10, inner delivery wire 24 and outer delivery wire 26 disposed within delivery catheter 200. Thus, medical device 10 is configured to be constrained from the expanded preset configuration to a reduced configuration for placement within delivery catheter 200. In one example, medical device 10 may be axially elongated from an expanded configuration to a reduced configuration, such as by displacing the proximal and distal ends of medical device 10 away from one another. Delivery catheter 200 is axially displaceable with respect to medical device 10, as well as inner 24 and outer 26 delivery wires.

Medical device 10 includes central engagement member 28, as described above in detail with respect to FIGS. 1-4A, along with a proximal clamp and a proximal engagement member (not shown). Inner delivery wire 24 is configured to be positioned through the proximal clamp and the proximal engagement member and coupled to central engagement member 28 such as with a threaded engagement (see e.g., FIGS. 1-4B). While holding inner delivery wire 24 stationary, delivery catheter 200 may be withdrawn in a proximal direction. In this manner, central engagement member 28 will remain in a desired position while medical device 10 is deployed. For example, central engagement member 28 may be aligned with the aortic valve. Upon withdrawing delivery catheter 200, medical device 10 is configured to expand from its reduced configuration towards its expanded configuration at the target site. Where medical device 10 is deployed at the aortic valve, proximal lobe 12 may be positioned proximal of the aortic valve outside of the heart, while distal lobe 14 is positioned distal of the valve and within the heart. Once medical device 10 is deployed in an expanded configuration and the position at the target site is satisfactory, inner deliver wire 24 may be detached from central engagement member 28. According to one embodiment, inner delivery wire 24 and outer delivery wire 26 are similar to the ITV-FX delivery system manufactured by AGA Medical Corporation.

Figure 30:
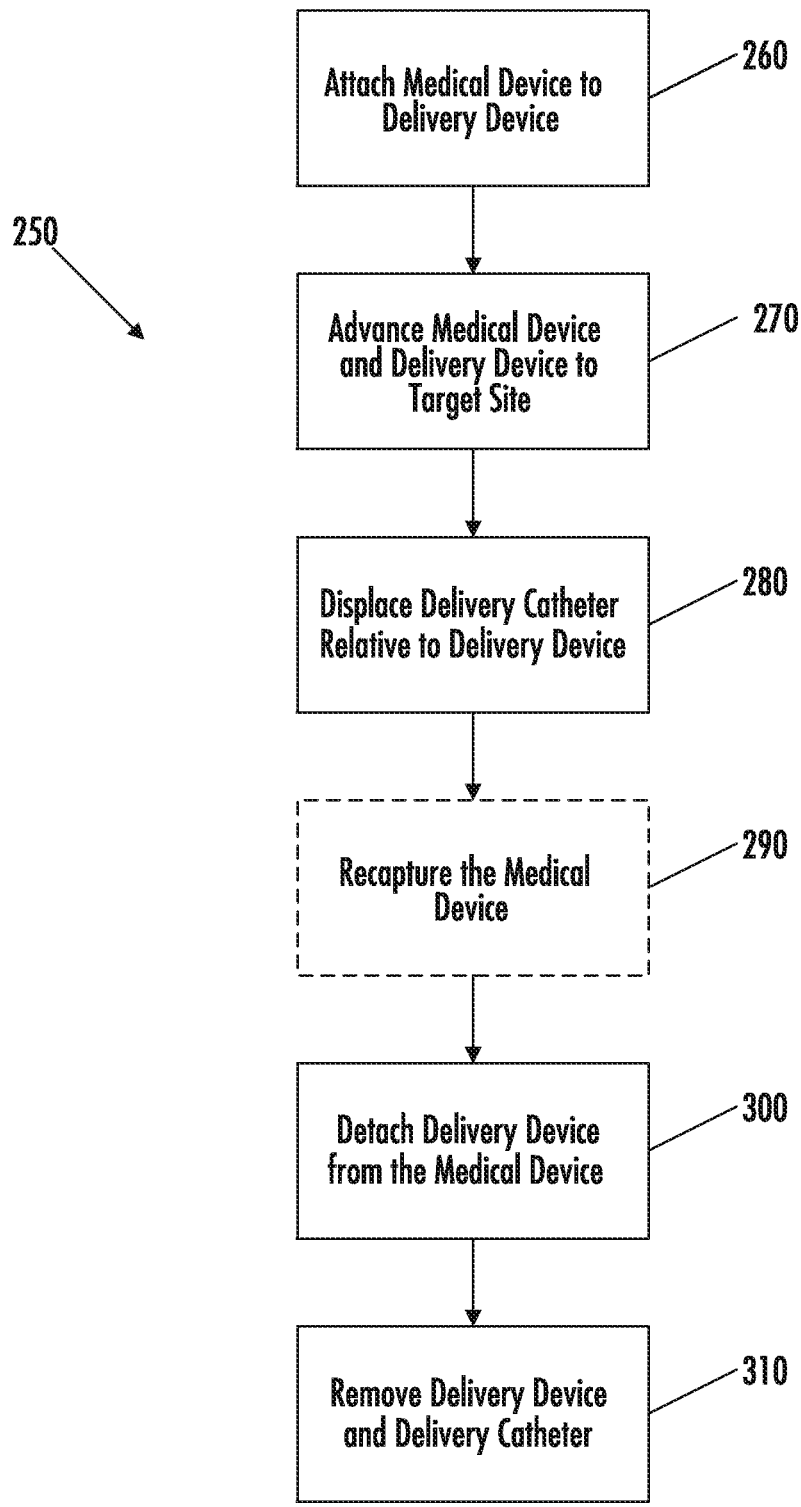
FIG. 30 is a flowchart illustrating a method of delivering a medical device according to an embodiment of the present disclosure.

In FIG. 30, a method (250) for delivering a medical device to a target site, such as medical device 10 described above, is summarized. A delivery device, such as delivery device 22 configured as described above in connection with one or more of FIGS. 1-4, 4A, 4B, 16, 18, 19, and 29 may be used to deliver the medical device. For example, the delivery device may include an inner delivery wire (see e.g., FIGS. 1-4A) and an outer delivery wire (see e.g., FIGS. 1, 2, 4, 4B), each configured to attach to and detach from the medical device.

The medical device may be attached to the delivery device, such as via attachment of the coupling member of the inner delivery wire to the medical device (Block 260). For example, the inner delivery wire may be attached to a central engagement member of the medical device (see e.g., FIG. 4A). Attachment of the medical device may occur, in some cases, at a facility at which the delivery device is manufactured, such that an operator of the delivery device receives the delivery device and the medical device already attached. Alternatively, the medical device may be attached to the delivery device at the time of use or implantation or at a separate location from where the delivery device is manufactured. The delivery device and the medical device may then be advanced through a delivery catheter to the target site while the medical device is in a reduced configuration (Block 270). The delivery catheter may then be displaced relative to the inner delivery wire to expand the medical device from the reduced configuration to the expanded configuration (Block 280). For example, the delivery device and medical device may be displaced such that the inner delivery wire is coupled to a central engagement of the medical device, and while holding the inner delivery wire stationary, the delivery catheter is withdrawn proximally to unsheathe the medical device and allow the medical device to expand towards the expanded configuration.

The medical device may then be detached from the delivery device (Block 300), and the delivery device and the delivery catheter may be withdrawn from the target site (Block 310). In some cases, the medical device may be recaptured by engaging an outer delivery wire of the delivery device to the medical device (Block 290), such as in cases where the medical device is to be repositioned (e.g., when the medical device is deployed in an incorrect location or could be more favorably positioned). Where the medical device includes a non-permeable membrane, acute occlusion may occur immediately after the medical device is deployed at the target site. In instances where the medical device comprises a braided fabric deployed within the body, over time thrombi will tend to collect on the surface of the braided strands when the medical device is deployed within a patient to facilitate long-term occlusion at the target site.

The method depicted in FIG. 30 and described above represents only one possible method for delivering a medical device for treating a target site. It is understood that the illustrated steps in FIG. 30 may be performed in any desired order and should not be limited to the illustrated embodiments. In some embodiments, certain ones of the steps described above may be modified, omitted, or further amplified. Furthermore, in some embodiments, additional optional steps may be included, some examples of which are shown in dashed lines in FIG. 30. Modifications, additions, omission, or amplifications to the steps above may be performed in any order and in any combination. The particular methods of manufacturing and delivery will depend on the desired configuration of the medical device, the patient's anatomy, the condition and location of the target site, the preferences of the practitioner, and/or other considerations.

A medical device configured according to the embodiments described above may provide for several advantages. For example, the medical device may be configured to cooperate with a delivery device to be more accurately deployed at the target site in a desired position due to engagement of inner delivery wire with central engagement member. In this regard, when engaged with the inner delivery wire, the central engagement member may be used by an operator to visualize the position of the medical device at the target site, and manipulation of the inner delivery wire while engaged with the central engagement member may facilitate placement at the target site. The medical device is also configured to be deployed at the target site so as to limit disruption of the anatomy surrounding the target site or injuring the target site. In particular, a medical device including a concave shape or lip prevents disruption of the left and right coronary arteries in a deployed position. In one particular embodiment, the medical device is configured to occlude an aortic valve, such as for treating aortic insufficiency following LVAD implantation due to the valve not fully closing. The medical device may be configured to occlude the aortic valve to prevent blood from leaking through the aortic valve in a reverse direction thereby reducing the incidence of regurgitation. In some embodiments, the medical device includes modular components which allow the medical device to be customized for particular target sites. In addition, the medical device is adapted to treat a variety of target sites, and in some instances may facilitate both acute and long-term occlusion. For example, the medical device may include a non-permeable membrane to facilitate short term occlusion, while a braided fabric may be used to facilitate long-term occlusion. In some embodiments, the medical device may be configured to be locked in an expanded position to improve retention at the target site to reduce the incidence of migration Many modifications and other embodiments of the disclosure set forth herein will come to mind to one skilled in the art to which these embodiments pertain having the benefit of the teachings presented in the foregoing descriptions and the associated drawings. Therefore, it is to be understood that the above-described embodiments are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A medical device for treating a target site, the medical device comprising:
    a proximal lobe and a distal lobe comprising a braided fabric material, at least one of a proximal surface of the proximal lobe or a distal surface of the distal lobe comprising an engagement member configured to securely engage a first portion of a delivery device therethrough, the proximal lobe comprising a central member formed from the braided fabric material and extending outwardly from the proximal surface in a proximal direction, wherein the central member is configured to be exposed to a flow of blood upon delivery of the medical device to the target site; and
    a central engagement member disposed between the proximal lobe and the distal lobe, wherein at least one of proximal strands of the distal lobe or distal strands of the proximal lobe are affixed longitudinally along an external surface of the central engagement member, the central engagement member configured to be threadably engaged by a second portion of the delivery device disposed within the first portion of the delivery device, for facilitating deployment of the proximal and distal lobes from the delivery device at the target site.

2. The medical device of claim 1, wherein the central engagement member comprises a threaded surface for threadably engaging the delivery device.

3. The medical device of claim 1, wherein the proximal lobe comprises the proximal surface, a distal surface, and an outer flange, and wherein the proximal surface and outer flange define a concave shape facing in a proximal direction.

4. The medical device of claim 1, wherein the proximal lobe has a larger outer diameter than the distal lobe.

5. The medical device of claim 1, wherein the proximal lobe comprises a different braid configuration than the distal lobe.

6. The medical device of claim 1, wherein the proximal lobe and distal lobe are formed from a tubular member having a proximal end and a distal end, the tubular member having an expanded configuration and configured to be constrained to a reduced configuration for delivery to the target site.

7. The medical device of claim 6, further comprising a pair of end clamps, one of the pair of end clamps secured to the proximal end of the tubular member and the other of the pair of end clamps secured to the distal end of the tubular member.

8. A system for delivering a medical device to a target site, the system comprising:
    a medical device comprising a central engagement member disposed between a proximal lobe and a distal lobe, wherein the proximal lobe and the distal lobe comprise a braided fabric material, and wherein at least one of proximal strands of the distal lobe or distal strands of the proximal lobe are affixed longitudinally along an external surface of the central engagement member; and
    a delivery device comprising an inner delivery wire disposed within an outer wire, and a coupling member fixedly coupled to the inner delivery wire and configured to couple to the central engagement member for facilitating deployment of the medical device from the delivery device at the target site,
    wherein at least one of a proximal surface of the proximal lobe or a distal surface of the distal lobe comprises an engagement member configured to securely engage the delivery device therethrough, and
    wherein the proximal lobe comprises a central member formed from the braided fabric material and extending outwardly from the proximal surface in a proximal direction, and wherein the central member is configured to be exposed to a flow of blood upon delivery of the medical device to the target site.

9. The system of claim 8, wherein the inner delivery wire is axially displaceable with respect to the outer delivery wire.

10. The system of claim 8, wherein the outer delivery wire is configured to engage the proximal or distal end of the medical device.

11. The system of claim 9, wherein the inner delivery wire is positioned through at least the proximal lobe.

12. The system of claim 9, wherein the coupling member of the inner delivery wire is configured to threadably engage and disengage the central engagement member in response to rotation of the inner delivery wire.

13. The system of claim 8, further comprising at least one end clamp secured to a proximal end of the proximal lobe.

14. The system of claim 13, wherein the at least one end clamp comprises a through hole, the through hole configured to receive the delivery device therethrough.

* * * * *

UNITED STATES PATENT AND TRADEMARK OFFICE
CERTIFICATE OF CORRECTION

| | |
|---|---|
| PATENT NO. | : 10,973,523 B2 |
| APPLICATION NO. | : 13/791337 |
| DATED | : April 13, 2021 |
| INVENTOR(S) | : Prom |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 174 days.

Signed and Sealed this
Sixth Day of December, 2022

Katherine Kelly Vidal
*Director of the United States Patent and Trademark Office*